US00PP19425P2

(12) United States Plant Patent
Snijder

(10) Patent No.: US PP19,425 P2
(45) Date of Patent: Nov. 4, 2008

(54) ***GERANIUM* PLANT NAMED 'FISUM ROSE EYE'**

(50) Latin Name: *Pelargonium×hortorum*
Varietal Denomination: Fisum Rose Eye

(75) Inventor: Ronald Christiaan Snijder, De Lier (NL)

(73) Assignee: Fides B.V., De Lier (NL)

( * ) Notice: Subject to any disclaimer, the term of this patent is extended or adjusted under 35 U.S.C. 154(b) by 168 days.

(21) Appl. No.: 11/633,120

(22) Filed: Dec. 1, 2006

(51) Int. Cl.
*A01H 5/00* (2006.01)

(52) U.S. Cl. ..... Plt./329

(58) Field of Classification Search ..... Plt./325, Plt./328, 329
See application file for complete search history.

*Primary Examiner*—Howard J Locker
(74) *Attorney, Agent, or Firm*—C. A. Whealy

(57) ABSTRACT

A new and distinct cultivar of Zonal *Geranium* plant named 'Fisum Rose Eye', characterized by its upright plant habit; freely basal branching habit; dark green-colored leaves; freely flowering habit; large semi-double red purple-colored flowers with slightly darker-colored central splotches; and good garden performance.

1 Drawing Sheet

Botanical designation: *Pelargonium×hortorum*.
Cultivar denomination: 'Fisum Rose Eye'.

BACKGROUND OF THE INVENTION

The present invention relates to a new and distinct cultivar of Zonal *Geranium*, botanically known as *Pelargonium×hortorum,* and hereinafter referred to by the name 'Fisum Rose Eye'.

The new Zonal *Geranium* is a product of a planned breeding program conducted by the Inventor in De Lier, The Netherlands. The objective of the breeding program is to create new freely-branching and freely-flowering Zonal *Geranium* cultivars with attractive foliage and flower coloration.

The new Zonal *Geranium* originated from a cross-pollination made by the Inventor in De Lier, The Netherlands of two unnamed selections of *Pelargonium×hortorum,* not patented, in August, 2003. The cultivar Fisum Rose Eye was discovered and selected by the Inventor as a flowering plant from within the progeny of the stated cross-pollination in a controlled environment in De Lier, The Netherlands, in March, 2004.

Asexual reproduction of the new Zonal *Geranium* by vegetative terminal cuttings in a controlled environment in De Lier, The Netherlands, since July, 2004, has shown that the unique features of this new Zonal *Geranium* are stable and reproduced true to type in successive generations.

SUMMARY OF THE INVENTION

The cultivar Fisum Rose Eye has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Fisum Rose Eye'. These characteristics in combination distinguish 'Fisum Rose Eye' as a new and distinct cultivar of Zonal *Geranium:*

1. Upright plant habit.
2. Freely basal branching habit.
3. Dark green-colored leaves.
4. Freely flowering habit.
5. Large semi-double red purple-colored flowers with slightly darker-colored central splotches.
6. Good garden performance.

Plants of the new Zonal *Geranium* differ primarily from plants of the parent selections in plant size and flower color.

Plants of the new Zonal *Geranium* can be compared to plants of the *Pelargonium×hortorum* cultivar Meridonna, disclosed in U.S. Plant Pat. No. 9,152. In side-by-side comparisons conducted in De Lier, The Netherlands, plants of the new Zonal *Geranium* differed from plants of the cultivar Meridonna in the following characteristics:

1. Plants of the new Zonal *Geranium* had smaller leaves than plants of the cultivar Meridonna.
2. Plants of the new Zonal *Geranium* were more freely flowering than plants of the cultivar Meridonna.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*. The photograph comprises a side perspective view of a typical flowering plant of 'Fisum Rose Eye' grown in a container.

DETAILED BOTANICAL DESCRIPTION

The aforementioned photograph and following observations, measurements and values describe plants grown in De Lier, The Netherlands in a glass-covered greenhouse during the winter and early spring and under conditions which closely approximate commercial production. During the production of the plants, day temperatures ranged from 14° C. to 20° C., night temperatures ranged from 8° C. to 18° C. and light levels ranged from 10,000 lux to 50,000 lux. Plants were about three months old when the photographs and the description were taken. In the detailed description, color references are made to The Royal Horticultural Society Colour Chart, 1995 Edition, except where general terms of ordinary dictionary significance are used.

Botanical classification: *Pelargonium×hortorum* cultivar Fisum Rose Eye.

Parentage:

*Female, or seed, parent.*—Unnamed selection of *Pelargonium×hortorum,* not patented.

*Male or pollen parent.*—Unnamed selection of *Pelargonium×hortorum,* not patented.

Propagation:

*Type.*—By vegetative terminal cuttings.

*Time to initiate roots, summer.*—About five to seven days at temperatures of 22° C.

*Time to initiate roots, winter.*—About five to ten days at temperatures of 22° C.

*Time to produce a rooted young plant, summer.*—About two to three weeks at temperatures of 20° C.

*Time to produce a rooted young plant, winter.*—About two to four weeks at temperatures of 20° C.

*Root description.*—Fine, fibrous.

*Rooting habit.*—Freely branching, moderately dense.

Plant description:

*General appearance.*—Upright plant habit; uniformly mounded; densely foliated.

*Growth and branching habit.*—Moderately vigorous growth habit. Freely basal branching habit with about five lateral branches developing per plant.

*Plant height, to top of umbels.*—About 15 cm to 25 cm.

*Plant width.*—About 12 cm to 20 cm.

*Lateral branches.*—Length: About 5 cm to 25 cm. Diameter: About 5 mm to 8 mm. Internode length: About 4 mm to 3 cm. Texture: Pubescent. Strength: Strong, sturdy. Color: 144C.

Foliage description:

*Arrangement.*—Alternate; simple.

*Length.*—About 5 cm.

*Width.*—About 6 cm to 9 cm.

*Shape.*—Orbicular.

*Apex.*—Rounded.

*Base.*—Cordate.

*Margin.*—Crenate; slightly undulate.

*Venation pattern.*—Palmate.

*Texture, upper and lower surfaces.*—Densely pubescent.

*Color.*—Developing foliage, upper surface: 143A; towards the base, 143C. Developing foliage, lower surface: 143C. Fully developed, upper surface: 137A; venation, 144A. Fully developed, lower surface: 137C; venation, 144B. Zonation pattern: Not observed.

*Petiole.*—Length: About 3 cm to 7 cm. Diameter: About 2 mm to 3 mm. Texture, upper and lower surfaces: Pubescent. Color, upper and lower surfaces: 143B.

Flower description:

*Flower arrangement.*—Semi-double rotate flowers arranged in rounded hemispherical umbels arising from apical leaf axils. Umbels displayed above the foliage on strong peduncles. Flowers face upright to outward. Flowers persistent. Flowers not fragrant.

*Quantity of flowers.*—Freely flowering habit; about 10 to 30 flower buds and open flowers per umbel.

*Flowering season.*—Year-round under greenhouse conditions. In the garden in De Lier, The Netherlands, flowering is continuous from late spring until frost in autumn.

*Flower longevity.*—Individual flowers last about two to eight days on the plant.

*Umbel height.*—About 5 cm to 8 cm.

*Umbel diameter.*—About 5 cm to 8 cm.

*Flower diameter.*—About 4 cm to 5 cm.

*Flower depth* (*height*).—About 4 cm to 5 cm.

*Flower buds.*—Length: About 5 mm to 7 mm. Diameter: About 4 mm to 6 mm. Shape: Globular to elliptic. Color: 143C.

*Petals.*—Quantity per flower: About five to ten. Length: About 2 cm to 3 cm. Width: About 1.5 cm to 2.5 cm. Shape: Spatulate to obovate. Apex: Rounded. Base: Attenuate. Margin: Entire. Texture, upper and lower surfaces: Smooth, glabrous. Color: When opening, upper surface: 74B. When opening, lower surface: 73C. Fully opened, upper surface: 74A; central splotch, close to 66A; towards the base, close to 155D; venation, 66A. Fully opened, lower surface: 75C.

*Petaloids.*—Quantity per flower: None to about five. Length: About 1 mm to 2 cm. Width: About 2 mm to 2 cm. Shape: Irregularly shaped; obovate to irregularly oblanceolate. Apex: Rounded. Base: Attenuate. Margin: Entire. Texture, upper and lower surfaces: Smooth, glabrous. Color: When opening, upper and lower surfaces: 74B. Fully opened, upper surface: 74A; central splotch, close to 66A; towards the base, close to 155D; venation, 66A. Fully opened, lower surface: 75C.

*Sepals.*—Quantity per flower: Five, arranged in a single whorl. Length: About 1.1 cm to 1.3 cm. Width: About 3 mm to 5 mm. Shape: Ovate, oblong. Apex: Acute. Base: Truncate. Margin: Entire. Texture, upper and lower surfaces: Densely pubescent. Color: Immature, upper and lower surfaces: 143A. Mature, upper and surface: 146A; towards the base, 185A; towards the margin, 180A. Mature, lower surface: 147A; towards the base, 185A; towards the margin, 180A.

*Peduncle* (*umbel stem*).—Length: About 7 cm to 15 cm. Diameter: About 3 mm. Strength: Strong. Angle: Erect to about 30° C. from vertical. Texture: Pubescent. Color: 143A.

*Pedicel* (*individual flower stem*).—Length: About 2 cm to 3 cm. Diameter: About 1 mm to 2 mm. Strength: Moderately strong. Angle: Erect to about 60° C. from vertical. Texture: Pubescent. Color: 183C.

*Reproductive organs.*—Androecium: Stamen quantity per flower: About one to ten. Filament length: About 4 mm to 8 mm. Filament color: Close to 155A. Anther length: About 2 mm to 3 mm. Anther shape: Oblong. Anther color: 184D. Pollen amount: Moderate. Pollen color: 170B. Gynoecium: Pistil quantity per flower: One. Pistil length: About 9 mm to 1.2 cm. Stigma shape: Tapering; reflexed. Stigma color: 74B. Style length: About 4 mm to 5 mm. Style color: 74B. Ovary color: 138D.

*Seed.*—Seed development has not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 0° C. to about 40° C. and have demonstrated good garden performance.

It is claimed:

1. A new and distinct Zonal *Geranium* plant named 'Fisum Rose Eye' as illustrated and described.

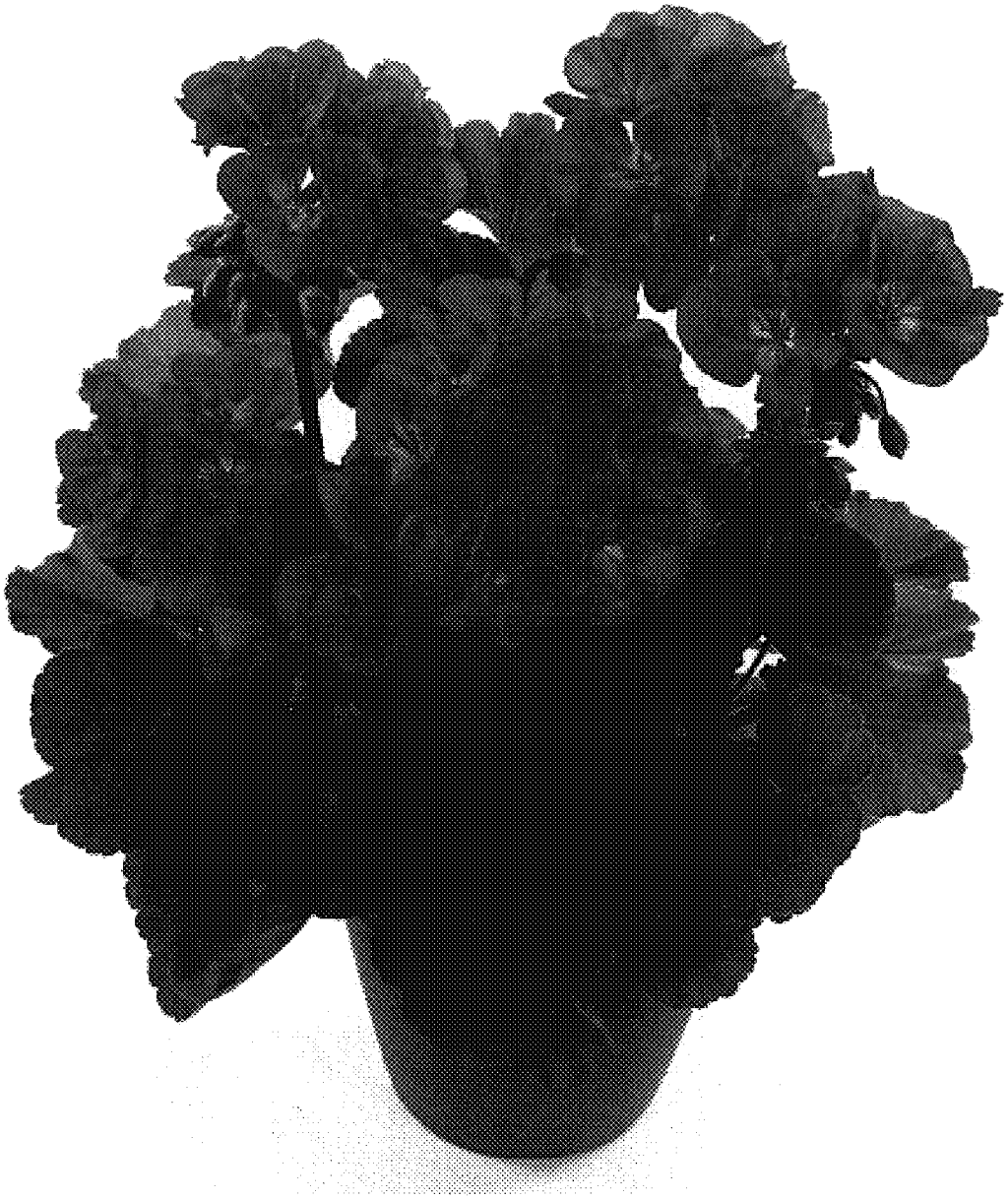

* * * * *